US011819303B2

(12) United States Patent
Mirtschin et al.

(10) Patent No.: US 11,819,303 B2
(45) Date of Patent: Nov. 21, 2023

(54) DAMAGE-RESISTANT GLOVES WITH BREACH-INDICATOR FUNCTION

(71) Applicant: SMARTERIALS TECHNOLOGY GMBH, Berlin (DE)

(72) Inventors: Nikolaus Mirtschin, Berlin (DE); Martin Bothe, Berlin (DE); Larisa Schmidt, Berlin (DE)

(73) Assignee: SMARTERIALS TECHNOLOGY GMBH, Berlin (DE)

( * ) Notice: Subject to any disclaimer, the term of this patent is extended or adjusted under 35 U.S.C. 154(b) by 1120 days.

(21) Appl. No.: 16/479,969

(22) PCT Filed: Jan. 23, 2018

(86) PCT No.: PCT/EP2018/051599
§ 371 (c)(1),
(2) Date: Jul. 23, 2019

(87) PCT Pub. No.: WO2018/138095
PCT Pub. Date: Aug. 2, 2018

(65) Prior Publication Data
US 2019/0374300 A1    Dec. 12, 2019

(30) Foreign Application Priority Data

Jan. 24, 2017  (EP) .................................... 17152932
Aug. 17, 2017  (WO) ................. PCT/EP2017/069954

(51) Int. Cl.
*A61B 42/30* (2016.01)
*A41D 19/00* (2006.01)
(Continued)

(52) U.S. Cl.
CPC .......... *A61B 42/30* (2016.02); *A41D 19/0006* (2013.01); *A41D 19/0096* (2013.01);
(Continued)

(58) Field of Classification Search
CPC ................ A41D 19/00; A41D 19/0006; A41D 19/0044; A41D 19/0055; A41D 19/0058;
(Continued)

(56) References Cited

U.S. PATENT DOCUMENTS 3,633,216 A     1/1972  Schonholtz
3,963,627 A *   6/1976  Cottrell ...................... B01J 2/30
                                                                         428/405
(Continued)

FOREIGN PATENT DOCUMENTS

AU      3979272     9/1973
CA      2448475     5/2004
(Continued)

*Primary Examiner* — Michael C Miggins
(74) *Attorney, Agent, or Firm* — JMB DAVIS BEN-DAVID

(57) ABSTRACT

The present invention relates to a multi-layered latex cover, particularly a glove, comprising a main body and a rim. The main body comprises an outer latex layer, an inner latex layer and an intermediate layer comprising particles. The rim essentially consists of the agglutinated outer and inner latex layer. The particles in the intermediate layer are chemically functionalized with a compound comprising hydrophobic groups. Prior to functionalization, the particles are characterized by a mean diameter of ≤100 μm and a surface comprising exposed OH groups. The invention further relates to a method of producing the multi-layered cover, comprising the steps of providing a former and sequentially immersing it in a first coagulator solution, a first latex dispersion, a particle suspension and a second latex dispersion.

18 Claims, 7 Drawing Sheets

(51) Int. Cl.
*B32B 1/02* (2006.01)
*B29C 41/14* (2006.01)
*A61B 42/10* (2016.01)
*B29C 41/22* (2006.01)
*B29D 99/00* (2010.01)
*C09C 3/12* (2006.01)
*B32B 5/16* (2006.01)
*B29K 105/00* (2006.01)
*B29L 31/48* (2006.01)
*C08J 5/02* (2006.01)
*C08K 3/36* (2006.01)

(52) U.S. Cl.
CPC ............. *A61B 42/10* (2016.02); *B29C 41/14* (2013.01); *B29C 41/22* (2013.01); *B29D 99/0067* (2013.01); *B32B 1/02* (2013.01); *B32B 5/16* (2013.01); *C09C 3/12* (2013.01); B29K 2105/0064 (2013.01); B29L 2031/4864 (2013.01); C08J 5/02 (2013.01); C08K 3/36 (2013.01)

(58) Field of Classification Search
CPC ............. A41D 19/0096; A41D 19/015; A41D 19/01505; A41D 19/01576; A61B 42/30; B29D 99/0067; B29L 2031/4864; B29K 2105/0064; C08J 5/02; C08K 3/36; B29C 41/14; B29C 41/16; B29C 41/18; B29C 41/22; B32B 1/02; B32B 1/08; B32B 5/00; B32B 5/16
See application file for complete search history.

(56) References Cited

U.S. PATENT DOCUMENTS

| | | | |
|---|---|---|---|
| 4,274,883 A | 6/1981 | Lumbeck et al. | |
| 4,696,065 A | 9/1987 | Elenteny | |
| 5,357,636 A | 10/1994 | Dresdner, Jr. et al. | |
| 5,459,879 A | 10/1995 | Fuchs | |
| 5,484,832 A * | 1/1996 | Garrett | C08G 18/3895 523/213 |
| 5,486,322 A | 1/1996 | Fuchs | |
| 5,549,924 A | 8/1996 | Shlenker et al. | |
| 5,679,399 A | 10/1997 | Shlenker et al. | |
| 5,817,433 A * | 10/1998 | Darras | A41D 19/0096 428/408 |
| 5,911,848 A | 6/1999 | Haber et al. | |
| 5,965,276 A | 10/1999 | Shlenker et al. | |
| 6,145,130 A | 11/2000 | Haber et al. | |
| 6,175,962 B1 | 1/2001 | Michelson | |
| 6,527,990 B2 | 3/2003 | Yamashita et al. | |
| 6,610,382 B1 * | 8/2003 | Kobe | A63B 60/06 428/104 |
| 6,618,861 B2 | 9/2003 | Saks et al. | |
| 7,585,526 B2 | 9/2009 | Hamann | |
| 8,522,363 B2 | 9/2013 | Hassan et al. | |
| 8,815,163 B2 | 8/2014 | Bangera et al. | |
| 9,308,048 B2 | 4/2016 | Venables et al. | |
| 2003/0021903 A1 | 1/2003 | Shlenker et al. | |
| 2003/0124354 A1 | 7/2003 | Maris | |
| 2004/0146717 A1 * | 7/2004 | Corzani | A41D 19/0058 428/423.1 |
| 2005/0222543 A1 | 10/2005 | Shao | |
| 2006/0026737 A1 | 2/2006 | Chen | |
| 2006/0191056 A1 * | 8/2006 | Bottcher | A41D 19/015 2/159 |
| 2008/0139723 A1 * | 6/2008 | Foo | A41D 19/0082 427/407.1 |
| 2011/0287553 A1 | 11/2011 | Hassan | |
| 2012/0296029 A1 * | 11/2012 | Liu | C08F 297/02 977/773 |
| 2013/0104284 A1 | 5/2013 | Kantrowitz | |
| 2015/0143608 A1 | 5/2015 | Loo et al. | |
| 2015/0274929 A1 * | 10/2015 | Brick | C08L 83/00 428/36.9 |
| 2016/0033418 A1 | 2/2016 | Eng et al. | |
| 2016/0160069 A1 | 6/2016 | Chen et al. | |
| 2017/0119485 A1 * | 5/2017 | Pham | A61B 42/30 |
| 2017/0218142 A1 | 8/2017 | Foo et al. | |

FOREIGN PATENT DOCUMENTS

| | | | |
|---|---|---|---|
| CN | 103665487 | 3/2014 | |
| DE | 68914941 | 8/1994 | |
| DE | 102005009826 | 9/2006 | |
| EP | 0511681 | 11/1992 | |
| EP | 0561651 | 9/1993 | |
| EP | 0592175 | 4/1994 | |
| EP | 0836392 | 4/1998 | |
| EP | 1131381 | 9/2001 | |
| EP | 1235673 | 9/2002 | |
| EP | 1742786 | 1/2007 | |
| EP | 1843672 | 10/2007 | |
| EP | 2152187 | 2/2010 | |
| EP | 2389820 | 11/2011 | |
| EP | 2407213 | 1/2012 | |
| EP | 2409586 | 1/2012 | |
| EP | 2253234 | 10/2015 | |
| GB | 1359162 | 7/1974 | |
| GB | 2270618 | 3/1994 | |
| GB | 2453000 | 3/2009 | |
| GB | 2493288 | 1/2013 | |
| JP | H 5-230702 A | 9/1993 | |
| JP | 2012531931 A | 12/2012 | |
| KR | 10-2012-0082391 | 7/2012 | |
| WO | 9514447 | 6/1995 | |
| WO | WO-2006/045012 A2 * | 4/2006 | ............. C09C 1/30 |
| WO | 2007068873 | 6/2007 | |
| WO | 2016011480 | 1/2016 | |
| WO | 2016090368 | 6/2016 | |
| WO | 2016115132 A1 | 7/2016 | |
| WO | 2017009033 | 1/2017 | |
| WO | 2017065599 | 4/2017 | |

* cited by examiner a)

b)

c)

DAMAGE-RESISTANT GLOVES WITH BREACH-INDICATOR FUNCTION

CROSS-REFERENCE TO RELATED APPLICATIONS

This is the U.S. National Stage of International Patent Application No. PCT/EP2018/051599 filed Jan. 23, 2018, which claims priority to European Patent Application No. 17152932.4 filed Jan. 24, 2017, and International Patent Application No. PCT/EP2017/069954 filed Aug. 7, 2017.

The present invention relates to disposable, multi-layered gloves and to a method of producing the same.

BACKGROUND

Disposable gloves have to meet many different, sometimes even conflicting demands. Gloves worn by health care professionals, laboratory and emergency personnel provide a physical barrier covering the bare hand as a hygiene and contamination protection measure. The gloves have to protect their wearer from direct skin contact with harmful substances and infectious agents. They have to be durable, but flexible and provide a good grip while not compromising the sense of touch too much. The gloves should also be non-irritant to the skin. Certain gloves, in particular surgical gloves, have to be sterile and individually wrapped. Since the gloves are frequently replaced, it is necessary for them to be relatively inexpensive while still exhibiting a high quality.

A certain percentage of gloves manufactured in mass production exhibit hole defects. To reduce the percentage of gloves with hole defects is an important challenge. Holes can also occur after the production process through unauthorized tampering or by accidents while using the glove, e.g. via damage by scalpels or needles. Unfortunately, these holes are usually not easily visible and thus not immediately noticed. To increase safety, a common approach is to don two gloves, one above the other. This however creates other problems, like slipping and sagging of the outer glove.

Double-layered gloves can provide the same physical barrier as wearing two gloves without the mentioned disadvantages. A very relevant feature of such a double-layered glove can be an indicator function that immediately notifies the wearer of a hole in one of the layers, e.g. by a visible signal.

Gloves usually consist of several agglutinated layers. These result from multiple dipping processes and cannot be distinguished from a single, thicker layer. However, modifications exist. EP 0 561 651 A1 (also published as U.S. Pat. Nos. 5,438,709 and 6,280,673) claims an efficient dipping process for a polyvinyl alcohol coating to achieve lubricious surface properties of the gloves. US 2003/0124354 A1 describes the dipping of the former in various steps, either by dipping in the same or a different material, or by dipping into latex baths of different colour. This and any other US patent document cited in the present specification are incorporated by reference herein.

The integration of a perforation indicator, which warns the user in case of breach, requires the spatial separation of the polymer layers. Methods of producing gloves with two separate layers are usually complex and expensive. Approaches to produce such latex articles in a single process are exemplarily described in U.S. Pat. No. 5,965,276. Here, particles such as gentian violet are applied in an additional dipping step in between the layers in order to separate the adjoining inner and outer layer. In another example, it proposes intermediate dipping into zinc stearate, claiming the same result. One problem is that this process requires another dipping into a coagulator. Another problem is that these substances are harmful to health. Since not being chemically linked to the latex layer, these substances may be stripped off or rinsed out. In case of breach of the glove, it may get in contact with the skin and open surgery and put patients at risk.

In another approach to achieve perforation indication, dyed microcapsules are employed in an intermediate layer (US 2011/0287553). WO2007068873 proposes the use of silica particles to form the intermediate layer. While a procedure using silica particles produces the desired effect of separating the layers, it fails to accomplish the quality behaviour of double gloving systems. A controlled application of the silica is difficult, the particles are not bound to the latex layers and their slight hydrophilicity does neither support the stabilization in a suspension for dipping, nor does it allow to homogeneously apply the particles to the hydrophobic latex layers.

Based on the above-mentioned state of the art, the objective of the present invention is to provide a cost-effective, fast and reliable method to produce durable, damage-resistant gloves comprising a breach-indicator function. This problem is solved by the subject-matter of the independent claims.

DESCRIPTION OF THE INVENTION

The term "latex" in the context of the present specification relates to a rubbery polymer. Non-limiting examples of latex rubber include natural rubber, caoutchouk, polyisoprene, nitrile-containing polymers, nitrile rubber, and polychloroprene.

The term "latex dispersion" relates to an aqueous polymer dispersion of one of the above named latices, that can be solidified.

Multi-Layered Cover

According to a first aspect of the invention, a multi-layered shaped cover is provided. In particular embodiments, the cover is shaped like a human hand and may serve as a glove. The multi-layered cover comprises a main body and a rim. The main body comprises an outer latex layer and a distinct inner latex layer separated from but adjacent to the outer layer on an inner side of the cover where the cover is glove-shaped. An intermediate layer comprising particles separates the outer and the inner layer. The rim essentially consists of the agglutinated first and second latex layer (FIG. 1). In the non-functionalized state, the particles are characterized by a mean diameter of 100 µm and a surface comprising exposed OH groups.

In the intermediate layer, the particles are chemically functionalized with a compound comprising hydrophobic groups.

Particles

In certain embodiments, the particles are micro particles. In certain embodiments, the particles are nano particles.

In certain embodiments, the particles are organic particles. In certain embodiments, the particles are organic particles comprising or essentially consisting of a material selected from polystyrene, polylactides (PLA), polyglycolides (PGA), poly(lactide co-glycolides) (PLGA), polyanhydrides, polyorthoesters, polycyanoacrylates, polycaprolactone, polyglutamic acid, polymalic acid, poly(N-vinyl pyrrolidone), poly(methyl methacrylate), poly(vinyl alcohol), poly(acrylic acid), poly acrylamide, poly(ethyleneglycol) and poly(methacrylic acid).

In certain embodiments, the particles are inorganic particles. In certain embodiments, the particles are inorganic particles comprising or essentially consisting of a material selected from silica, titanium dioxide, zirconium dioxide, iron oxide, gold, silver, gadolinium, magnesium fluoride, strontium fluoride, or similar fluorides.

In certain embodiments, the particles comprise or essentially consist of silica, titanium dioxide or zirconium dioxide. In certain embodiments, the particles comprise or essentially consist of silica.

In certain embodiments, the particles are characterized by a mean diameter of ≤10 μm. In certain embodiments, the particles are characterized by a mean diameter of ≤1 μm. In certain embodiments, the particles are characterized by a mean diameter of ≤0.1 μm.

In certain embodiments, the particles are melamine resin particles. In certain embodiments, the particles are polystyrene particles. In certain embodiments, the particles are polymethylmethacrylate particles. In certain embodiments, the particles are zeolitic imidazolate frameworks (ZIFs). ZIFs are composed of tetrahedrally-coordinated transition metal ions (e.g. Fe, Co, Cu, Zn) connected by imidazolate linkers. In certain embodiments, the particles are carbon nanotubes. In certain embodiments, the particles are graphene particles.

In certain embodiments, the particles are silica particles, particularly silica particles having a mean diameter of ≤50 μm, particularly silica particles having a mean diameter of ≤25 μm, more particularly silica particles having a mean diameter of ≤15 μm. In certain embodiments, the silica particles have a mean diameter of 0.01 μm≤d≤1 μm. In certain embodiments, the silica particles are a mixture of smaller particles (0.01 μm≤d≤1 μm) and bigger particles (5 μm≤d≤25 μm).

The particles act as "spacers" between the latex layers and thus ensure separation between the two layers (FIG. 3). Another advantage of the particles is that they can add protection against stabs or cuts, since they are significantly harder than latex. The particles cover the surface of the first latex covered former until immersion depth $d_3$.

In certain embodiments, the particles, irrespective of material, have a mean diameter of ≤15 μm. In certain embodiments, the particles have a mean diameter of 10 μm. In certain embodiments, the particles have a mean diameter of 0.01 μm≤d≤0.1 μm. In certain embodiments, the particles have a mean diameter of 0.1 μm≤d≤1 μm. In certain embodiments, the particles are a mixture of smaller particles (0.1 μm≤d≤1 μm) and bigger particles (5 μm≤d≤25 μm). A particle diameter <10 μm increases particle stability in suspension.

In certain embodiments, the particles are characterized by a mean diameter of ≤100 μm. In certain embodiments, the particles are characterized by a mean diameter of 10 μm to 100 μm. In certain embodiments, the particles are characterized by a mean diameter of 20-50 μm. In certain embodiments, the particles have a mean diameter of ≤25 μm. Particles of the sizes mentioned in the range of 1 to 100 μm, particularly from 20 to 50 μm, can bring advantages in certain embodiments by creating larger cavities between the layers, facilitating the flow of liquid between the layers in the event of a breach.

In certain embodiments, the particles are coloured. Coloured particles increase the visibility of a perforation of the outer layer (indicator function).

The term "mean diameter" with regard to the particles particularly refers to the arithmetic mean or to the median of the diameter distribution of the particles. Such mean size may be determined by methods known to the skilled person such as, for example, by scanning electron microscopy, static or dynamic light scattering (SLS, DLS) or size-exclusion chromatography. If no other method is explicitly mentioned, particle sizes given herein to define the invention are deemed to be determined by dynamic light scattering.

In certain embodiments, the particles are characterized by a surface comprising exposed OH groups having a density of 1-10 m/nm². In certain embodiments, the particles are characterized by a surface comprising exposed OH groups having a density of 2-5/nm². In certain embodiments, the particles are characterized by a surface comprising exposed OH groups having a density of 2.2-2.5/nm². In certain embodiments, the particles are characterized by a surface comprising exposed OH groups having a density of 2.2/nm².

In certain embodiments, the particles are characterized by a surface comprising exposed SiOH (silanol) groups having a density of 2-5/nm². In certain embodiments, the particles are characterized by a surface comprising exposed SiOH groups having a density of 2.2-2.5/nm².

Free silanol groups can be quantified by various methods. By way of non-limiting example, methods for determining the SiOH concentration are: chlorinating ≡SiOH, reacting ≡SiOH with phenyllithium, diazomethane and alkylmagnesium halides, reacting ≡SiOH with $B_2H_6$, reacting ≡SiOH with $LiAlH_4$, infrared spectroscopy. A precise and straightforward method of quantifying the SiOH concentration on the particle surface is reacting particles with $LiAlH_4$ in accordance with the following equation in the presence of diglyme:

$$4SiOH+LiAlH_4 \rightarrow LiOSi+Al(OSi)_3+4H_2$$

This method involves measuring pressure to determine the amount of hydrogen formed and thus the silanol group density. As the hydride ion, functioning as an aggressive agent, is very small and highly reactive, all the silanol groups on the surface are detected, including the bridged ones. Unless stated otherwise, Si—OH densities stated herein are determined by this method Particle Functionalization The particles are functionalized with hydrophobic groups, or hydrophobic and hydrophilic groups. Functionalized particles may be in the form of monofunctional particles (functionalized with a specific hydrophobic group), multifunctional particles (functionalized with different hydrophobic, or hydrophobic and hydrophilic groups), or may be provided as a particle mixture comprising different monofunctional particles.

Functionalization with hydrophobic groups/with a hydrophobic layer enables/assists adhesion to the first latex covered former during application of the particles and anchoring/coupling to the latex during subsequent vulcanization. In certain embodiments, this is effected by the formation of covalent bonds between functionalized particle and latex.

Linking the particles to the latex ensures that in the case of breach of a latex layer the structural integrity of the product is granted and the particles are not released.

In certain embodiments, the particles are functionalized with a compound comprising unsaturated groups or sulfur, in particular with a compound selected from 7-octenyltrimethoxysilane, 5-hexenyltrimethoxysilane, 3-mercaptopropyltrimethoxysilane, 3-aminopropyl)triethoxysilane, tris(2-methoxyethoxy)(vinyl)silane, allyltrimethoxysilane, 3-(aminopropyl)triethoxysilane, hexadecyltrimethoxysilane, vinyltrimethoxysilane, triethoxyvinyl silane, 3-trimethoxysilylpropane-1-thiol, bis[3-(triethoxysilyl)propyl]tetrasulfide, 3-(methacryl oxypropyl)trimethoxysilane and 3-N-(3-triethoxysilylpropyl)gluconamide.

In certain embodiments, the functionalized particles have a hydrophobic particle surface.

In certain embodiments, the particles are additionally functionalized with a compound comprising hydrophilic groups. In certain embodiments, the particles are additionally functionalized with a compound comprising hydrophilic groups selected from polyethylene glycol, N-(3-triethoxysilylpropyl)gluconamide and/or 3-[methoxy(polyethyleneoxy) propyl]trimethoxysilane.

Functionalization with hydrophilic groups/with a hydrophilic layer improves the dispersibility of the particles in water and stabilizes the particles in an aqueous suspension. It also acts as a coagulating agent during the subsequent latex dipping, facilitating an even application of the latex layer on top.

Functionalization with hydrophilic groups/with a hydrophilic layer also improves the indicator function of the intermediate layer. A hydrophilic particle surface enables influx of aqueous liquids into the intermediate layer, such that the intermediate layer acts as a liquid reservoir in case of breach. By increasing the wettability in water, the water (or moisture from the environment) is sucked into the intermediate layer more efficiently and thereby the visible spot increases faster and spreads to a larger area. The filling level of the liquid reservoir becomes more apparent, when the inner layer is of dark colour.

Using the measuring instructions described in the examples section, the effect of differently modified particles in the intermediate layer on the effectiveness of the perforation indicator can be assessed. If a visibly discernible area indicating breach by change of colour of 50 mm² forms within 100 sec, this is considered a good perforation indicator (FIG. 9).

In certain embodiments, the functionalized particles have an amphiphilic particle surface.

An amphiphilic particle surface has advantages of both a hydrophobic particle surface and an hydrophilic particle surface. It allows stabilization or sufficient stabilization of the particles in an aqueous suspension, adhesion to the first latex covered former, serves as coagulating agent for application of the second latex cover, and assists chemical bonding to the latex cover during vulcanization. Amphiphilic particles enable an influx of aqueous liquids in case of breach, such that the intermediate layer acts as a liquid reservoir.

In certain embodiments, the functionalized particles are functionalized with at least two different substances.

The first substance is selected from substances suitable for yielding a hydrophobic surface. In certain embodiments, the first substance is selected from substances containing unsaturated groups or sulfur, more particularly a substance selected from 7-octenyltrimethoxysilane, 5-hexenyltrimethoxysilane, 3-mercaptopropyltrimethoxysilane, 3-aminopropyl)triethoxysilane, tris(2-methoxyethoxy)(vinyl)silane, allyltrimethoxysilane, 3-(aminopropyl)triethoxysilane, hexadecyltrimethoxysilane, vinyltrimethoxysilane, triethoxyvinylsilane, 3-trimethoxysilylpropane-1-thiol, bis[3-(triethoxysilyl)propyl]tetrasulfide, 3-(methacryloxypropyl)trimethoxysilane and 3-N-(3-triethoxysilylpropyl)gluconamide.

The second substance is selected from substances suitable for yielding a hydrophilic surface. In certain embodiments, the second substance is selected from polyethylene glycol and N-(3-triethoxysilylpropyl)gluconamide or 3-[methoxy(polyethyleneoxy)propyl]trimethoxy silane.

In certain embodiments, the particles comprise an alkylsilane surface coating. Within the context of the present specification, the term "silanes" refers to saturated chemical compounds consisting of a skeletal structure of silicon atoms (silicon backbone) and hydrogen. The silicon atoms are linked to each other as the tetrahedral centers of multiple single bonds. Each silicon atom has four bonds (either Si—H or Si—Si bonds), and each hydrogen atom is joined to a silicon atom (H—Si bonds). Commercially available silanes are synthetically derived. Within the context of the present specification, the term "alkylsilanes" refers to chemical compounds derived from silanes containing one or more alkyl groups. Non-limiting examples of alkylsilanes are methylsilane, trimethyl(trifluoromethyl)silane, trimethylsilanecarbonitrile, dimethylsilane, trimethylsilane, triethylsilane, tetramethylsilane and hexamethyldisilane.

In certain embodiments, silanes with long hydrophobic groups and unsaturated bonds such as tris(2-methoxyethoxy)(vinyl)silane, 7-octenyltrimethoxysilane, 5-hexenyltrimethoxysilane or allyltrimethoxysilane are used to achieve hydrophobicity of the particles. The vinyl group is used for covalent bonding of the particles to the polyisopren chain during vulcanization.

In certain embodiments, silanes comprising a thiol moiety (—SH), e.g. 3-mercaptopropyltrimethoxysilane, are used to achieve hydrophobicity of the particles. The thiol (mercapto) moiety is used for covalent attachment of the particles to the polyisoprene chain during vulcanization.

In certain embodiments, the particles are silica particles. In certain embodiments, the silica particles comprise an alkylsilane surface coating. An exemplary protocol for the functionalization of silica particles with tris(2-methoxyethoxy)(vinyl)silane as silane is given in the examples section below.

In certain embodiments, different monofunctional silica particles are applied subsequently or simultaneously (as a mixture).

An exemplary protocol for the functionalization of silica particles with either PEG or silanes is given in the examples section below.

In certain embodiments, hydrophilic monofunctional silica particles (functionalized with a specific hydrophilic group) are additionally functionalized with hydrophobic silanes, resulting in multifunctional particles that are functionalized with hydrophobic and hydrophilic groups.

In certain embodiments, silica particles functionalized with PEG, N-(3-triethoxysilylpropyl)gluconamide or 3-[methoxy(polyethyleneoxy)propyl]trimethoxysilane (hydrophilic) are additionally functionalized with hydrophobic silanes, particularly with a hydrophobic silane selected from methylsilane, trimethyl(trifluoromethyl)silane, trimethylsilanecarbonitrile, dimethylsilane, trimethylsilane, triethylsilane, tetramethylsilane, hexamethyldisilane, tris(2-methoxyethoxy)(vinyl)silane, 7-octenyltrimethoxysilane, 5-hexenyltrimethoxysilane, 3-mercaptopropyltrimethoxysilane and/or allyltrimethoxysilane. This second functionalization results in multifunctional particles that are functionalized with hydrophobic and hydrophilic groups.

In certain embodiments, the particles are multifunctional particles that are functionalized with hydrophobic and hydrophilic groups. In certain embodiments, the particles are bifunctional particles that are functionalized with hydrophobic and hydrophilic groups. In certain embodiments, the particles are multifunctional or bifunctional particles functionalized with PEG and silanes, particularly with PEG and a silane selected from methylsilane, trimethyl(trifluoromethyl)silane, trimethylsilanecarbonitrile, dimethylsilane, trimethylsilane, triethylsilane, tetramethylsilane, hexamethyldisilane, tris(2-methoxyethoxy)(vinyl)silane, 7-octenyltrimethoxysilane, 5-hexenyltrimethoxysilane, 3-mercaptopropyltrimethoxysilane, bis[3-(triethoxysilyl)propyl]tetrasulfide and/or allyltrimethoxysilane (FIG. 8).

In certain embodiments, silica particles are functionalized with PEG and a hydrophobic silane, in particular vinylsilane.

An exemplary protocol for the functionalization of silica particles with both PEG and silanes is given in the examples section below.

In certain embodiments, the PEG has a molecular weight of 200. In certain embodiments, the PEG has a molecular weight of 2000. In certain embodiments, the PEG has a molecular weight of 10,000. In certain embodiments, the PEG has a molecular weight of 20,000. In certain embodiments, the PEG has a molecular weight of more than 20,000. In certain embodiments, a mixture of PEG with different molecular weight is used. In certain embodiments, the PEG is a monodisperse PEG (mdPEG).

In certain embodiments, the silane is tris(2-methoxyethoxy)(vinyl)silane. In certain embodiments, the silane is allyltrimethoxysilane. In certain embodiments, the silane is 3-(aminopropyl)triethoxysilane. In certain embodiments, the silane is hexadecyltrimethoxy silane. In certain embodiments, the silane is vinyltrimethoxysilane. In certain embodiments, the silane is triethoxyvinylsilane. In certain embodiments, the silane is 3-trimethoxysilylpropane-1-thiol. In certain embodiments, the silane is bis[3-(triethoxysilyl)propyl]tetrasulfide. In certain embodiments, the silane is 3-(methacryloxypropyl)trimethoxysilane. In certain embodiments, the silane is 3-[methoxy(polyethyleneoxy)propyl]trimethoxysilane. In certain embodiments, the silane is N-(3-triethoxysilylpropyl)gluconamide.

In certain embodiments, particles functionalized with silane are chemically linked to the first latex layer. The former covered with the first latex layer is dipped into the prepared particle suspension. The particles adhere to the latex. The adhesion is increased due to the hydrophobicity of the silane coated particles. Subsequently, the functional groups on the outer surface of the particles are removed by dipping the latex and particle covered former into a sodium hydroxide solution (1 mol l$^{-1}$). To clean the particle-covered surface from the solution, it is dipped into a washing solution, which can be water or ethanol or a mixture thereof. A sample with a similarly treated latex surface is shown in FIG. 6. As a result, the silica particles surface is covered with Si—O—H-groups and thereby regains their hydrophilicity on the outer side. The particles outer surface functionalization is erased. When dipping into the second latex dispersion, sticking or adhesion of the particles to the second latex layer is prevented. The result is a multi-layered cover with particles linked to the first latex layer.

In certain embodiments, multifunctional particles are chemically linked to the first or second (inner and/or outer) latex layer. The particles are linked to the face of the latex facing the inner (intermediate) layer. The former covered with the first latex layer is dipped into the prepared particle suspension. The particles adhere to the latex and are chemically linked to the latex during vulcanization. Due to their hydrophilic functionalities, the particles optimize the surface for wettability. That way, good perforation indication is ensured. The contact angle with water for treated latex surfaces are shown in FIG. 10. A contact angle <90° is required for the perforation indicator to work; smaller contact angles of <45° are desirable. For the perforation indicator to perform within a reasonable amount of time, said contact angles are to be reached within a small amount of time, i.e. 10 s.

In certain embodiments, the silica particles are chemically linked to the second latex layer using silanes with hydrophobic groups. In certain embodiments, these silanes are tris(2-methoxyethoxy)(vinyl)silane or 7-octenyltrimethoxysilane. In certain embodiments, the silica particles are chemically linked to the second latex layer using unsaturated bonds. In certain embodiments, the silica particles contain amine groups for chemical attachment.

In certain embodiments, (3-aminopropyl)triethoxysilane-coated particles are covalently linked to the latex surface in an extra step. Using UV-radiation, 5-azido-2-nitrobenzoic acid n-hydroxysuccinimide ester is photo-crosslinked to the polyisopren's unsaturated bonds. The such functionalized polyisopren is exposed to the coated particles, resulting in the formation of bonds between the 5-azido-2-nitrobenzoic acid n-hydroxysuccinimide ester and the amine group.

To summarize, particles entrapped by elastomer layers manufactured via dip coating ideally
 are stabilized in a preferably aqueous suspension for initial application to a latex layer,
 adhere to the latex layer during dip coating,
 act as a coagulator during subsequent latex dipping,
 bond to the latex for safety purpose, and
 support liquid flow within the particle layer and enable a perforation indicator.

General

In certain embodiments, the multi-layered cover is characterized by a thickness of 100 μm to 800 μm uniformly extending across its entire dimensions.

Together, the outer latex layer and the inner latex layer have a thickness of at least 100 μm extending across the entire dimensions of the multi-layered cover. In certain embodiments, the outer and the inner latex layer are both characterized by a thickness of 50 μm uniformly extending across their entire dimensions. In certain embodiments, the outer and the inner latex layer are both characterized by a thickness of 30 μm to 70 μm, in particular 40 μm to 60 μm, uniformly extending across their entire dimensions, while together, they exhibit a thickness of at least 100 μm. In certain embodiments, the outer latex layer is characterized by a thickness of 40 μm uniformly extending across its entire dimensions and the inner latex layer is characterized by a thickness of 60 μm uniformly extending across its entire dimensions. In certain embodiments, the outer latex layer is characterized by a thickness of 60 μm uniformly extending across its entire dimensions and the inner latex layer is characterized by a thickness of 40 μm uniformly extending across its entire dimensions.

In certain embodiments of this aspect of the invention, the outer latex layer is characterized by a thickness of 100 μm to 500 μm uniformly extending across its entire dimensions and the inner latex layer is characterized by a thickness of 80 μm to 300 μm uniformly extending across its entire dimensions. In certain embodiments of this aspect of the invention, the outer latex layer is characterized by a thickness of approx. 200 μm uniformly extending across its entire dimensions and the inner latex layer is characterized by a thickness of approx. 100 μm uniformly extending across its entire dimensions.

Within the scope of the present invention are also latex covers that are fortified at certain positions, such as—in instances where the latex cover is a glove—the inner and outer surfaces of the fingers with or without the tips or the thenar eminence (the area at the base of the thumb), and/or the palm of the hand. In these positions, the thickness of the latex layers, in particular of the outer latex layer, may exceed the thickness that extends across the remaining dimensions of the latex cover. In certain embodiments, the thickness in these fortified areas is approx. 1.5×the thickness in other parts. In certain embodiments, the thickness in these fortified areas is approx. twice the thickness in other parts. In certain embodiments, increasing the thickness at certain positions is achieved by local application of an additional amount of latex solution. In certain embodiments, the increase in thickness is achieved by local application of a coagulant solution with a higher concentration of coagulator than said first (or said second) coagulator liquid, which leads to the formation of a thicker latex layer (compare diagram A). The application of the coagulant solution can be applied or removed in a dipping process and with tissue/brush.

In certain embodiments, outer layer and the inner latex layer are agglutinated at discrete regions. In certain embodiments, the discrete regions are regions of 1 mm² to 5 cm² at each fingertip. In certain embodiments, the discrete regions are regions of 4 mm² to 2.5 cm². In certain embodiments, the discrete regions are regions of 9 mm² to 1 cm² at each fingertip. In certain embodiments, the discrete regions are regions of approx. 25 mm² at each fingertip.

In certain embodiments, the discrete regions form patterns, signs, characters or numbers to indicate the size of the gloves, the lot number, the date of production or expiration, labels of authorities or company logos.

In certain embodiments, the intermediate layer comprises a plurality of layers. The plurality of layers within the intermediate layer comprises pairs of a particle layer and a latex layer. The particle layer comprises particles that chemically functionalized with a compound comprising hydrophobic groups. Prior to their functionalization, the particles have a mean diameter of 100 μm and a surface comprising exposed OH groups.

In certain embodiments, the intermediate layer comprises a plurality of double layers as described in the previous paragraph, and the inner latex layer, or the inner latex layer and adjacent latex layers of the intermediate layer are intentionally perforated. This results in a reservoir able to absorb aqueous liquid. In instances where the multi-layered cover is a glove, a perforated inner latex layer offers the advantage that moisture (e.g. sweat) can be transported from the skin to the intermediate layer of the glove via capillary action. This prevents slipping of the glove and thus improves grip security and safety of all actions performed while using the glove. The skilled person is aware that such a glove only has a perforation indicating function when it comprises two intact latex layers separated by an intermediate layer comprising particles.

In certain embodiments of this aspect of the invention, the multi-layered cover comprises a means for breach indication (a breach indicator function). The breach indicator function notifies the user of the multi-layered cover (e.g. the person wearing a double-layered latex glove according to the invention) of a perforation in one of the latex layers, usually the outer layer. By way of non-limiting example, the breach indicator function can be triggered by capillary action between the outer and the inner latex layer after perforation of one layer. The occurrence of a breach can be communicated in the form of a visible effect (agglutination of the outer and inner latex layer, described above) or in the form of an acoustic signal (enabled by RFID technology, see below).

In certain embodiments of this aspect of the invention, the multi-layered cover comprises a means for position tracking. The means for position tracking notifies the user of the multi-layered cover (e.g. the person wearing a double-layered latex glove according to the invention) if the multi-layered cover is located outside a predetermined area. This can be communicated in the form of an acoustic signal (enabled by RFID technology, see below).

In certain embodiments of this aspect of the invention, the intermediate layer comprises an RFID (radio frequency identification) tag. In the context of the present specification, an RFID tag is a device that can provide information about an object (to which the tag is attached) to an RFID reader using electromagnetic fields. The RFID reader transmits an encoded radio signal to interrogate the tag. The RFID tag receives the message and then responds with its identification and specific information. In the context of the present specification, an RFID tag can be used to obtain information on the perforation of the outer latex layer (breach indicator function). The tag can also be used to obtain information on the position of the protective latex cover. This is important in instances where a certain latex cover (e.g. a surgical glove used during an operation) may not leave a certain area (e.g. a sterile zone). The user can be notified about a change in position or a perforation by an acoustic signal. This can be an advantage if an optical signal is less likely to be noticed (e.g. soiled gloves).

In certain embodiments of this aspect of the invention, said outer layer and said inner latex layer are agglutinated at discrete regions, in particularly at regions of approx. 25 mm² at each fingertip.

Glove

According to a second aspect, the invention provides a glove comprising or essentially consisting of a multi-layered cover according to the first aspect of the invention.

Method

According to a third aspect, the invention provides a method of producing a multi-layered cover. The method comprises the steps of:
  a. Providing a former. The former is the negative of the latex cover that is to be produced, and resembles in shape the object or body part that is to be covered by the latex cover when the latter is employed in practice. In certain embodiments, the former is made of glazed or unglazed ceramic.
  b. Immersing the former in a first coagulator liquid to an immersion depth $d_1$, then retracting and drying the former. The different immersion depths during the dipping process are illustrated in FIG. 1.
  c. Immersing the former in a first latex dispersion to an immersion depth $d_2$, then retracting and drying the former. This step yields a first latex covered former. The latex layer established in this step is the first latex layer (FIG. 2: numeral 3).

d. Applying chemically functionalized particles to the first latex covered former to an immersion depth $d_3$. This step yields a particle treated former. The particles are chemically functionalized with a compound comprising hydrophobic groups.

In the non-functionalized state, the particles are characterized by
  a mean diameter of 100 μm and
  a surface comprising exposed OH groups. In certain embodiments, the latex covered former is immersed in a suspension of functionalized particles to an immersion depth $d_3$, then it is retracted and dried. In certain embodiments, the latex covered former is subsequently immersed in two or more different particle suspensions to an immersion depth $d_3$, then it is retracted and dried. These different particle suspensions may each comprise particles of different material and/or size, or particles functionalized with various groups. In certain embodiments, the suspension of particles comprises 9.4% (v/v) particles in water or ethanol or a mixture of water and ethanol. In certain embodiments, immersion in the suspension of particles is carried out for 1 to 10 seconds, in particular 2 to 3 seconds at room temperature.

In certain embodiments, the dipping process in the suspension is repeated, with or without intermediate heating.

In certain embodiments, the latex covered former is immersed in a second coagulator liquid to an immersion depth $d_3$, then it is retracted, the particles are applied to the immersed surface, and the particle treated former is dried.

e. Immersing the particle treated former in the second latex dispersion to an immersion depth $d_4$, then retracting and drying the particle treated former. This step yields a second latex covered former. The latex layer established in this step is the second latex layer (FIG. 2: numeral 5).

The immersion depths during the dipping process are specified as $d_1 \geq d_2 > d_3$ and $d_1 \geq d_4 > d_3$ (FIG. 1).

$d_1 \geq d_2$: The complete former surface to be immersed in the first latex dispersion is pre-treated with the first coagulation liquid. This supports homogenous hardening of the latex and (since the coagulation liquid comprises a former release agent) ensures an easy (future) removal of the multi-layered cover from the former.

$d_2 > d_3$ and $d_4 > d_3$: Only part of the first latex layer is treated with silica particles. The complete first latex layer—comprising a treated area and a non-treated area—is immersed in the second latex dispersion. In the treated area, agglutination of the first and second latex layers is prevented, resulting in two separate latex layers (lower circle in FIG. 2). In the non-treated area, the first and second latex layers agglutinate and form a single latex layer (upper circle in FIG. 2).

The rim is defined by the dipping depths of $d_2$, $d_3$ and $d_4$. In case of $d_2 = d_4$, the rim exclusively consists of agglutinated layers. Agglutinated and separated areas are also illustrated in FIG. 4.

In case of $d_2 > d_4$, said rim is extended by a single latex layer, resulting from dipping in the first latex dispersion. In case of $d_2 < d_4$, said rim is extended by a single latex layer, resulting from dipping in the second latex dispersion. In case of $d_2 \neq d_4$, said single latex layer has the colour of the respective dispersion.

f. Applying a coating to the second latex covered former, yielding a coated former. This step enables easy donning of the latex cover that is produced by the inventive method. By way of non-limiting example, this step comprises procedures selected from applying talcum powder, applying starch, coating with a polymer or performing a mild chlorination step. Coating with a polymer comprises adding a thin polymer layer which lubricates the latex cover. Chlorination comprises exposure of the second latex covered former to chlorine (as a chlorine acid mixture or as a chlorine gas) to make the latex harder and slicker.

g. Removing the applied layers from the coated former, thereby turning the first latex layer into the outer latex layer and the second latex layer into the inner latex layer. This step yields the multi-layered cover according to the invention.

In certain embodiments, the particles are characterized by a surface comprising exposed OH groups having a density of 2-5/nm$^2$. In certain embodiments, the particles are characterized by a surface comprising exposed OH groups having a density of 2.2-2.5/nm$^2$.

In certain embodiments, step d is effected by immersing the first latex covered former in an aqueous suspension comprising chemically functionalized particles to an immersion depth $d_3$. In certain embodiments, the concentration of chemically functionalized particles in the aqueous suspension is 0.5 mol %.

In certain embodiments, the chemically functionalized particles are applied in step d from an aqueous suspension with a concentration of 0.2 and 7 mol/L, particularly approx. 1 mol/L by adding a latex dispersion (40-80 wt %, particularly 60 wt % solid content) with a volume ratio of suspension to latex dispersion of less than 1:20. Latex being a part of the particle suspension can aid in facilitating adherence of the particles during the immersion step.

In certain embodiments, in steps b, c and e, immersion is carried out for 5 to 10 minutes each, at a temperature between 50° C. and 70° C. In certain embodiments, immersion is carried out for 5 to 10 minutes each, at approx. 60° C.

In certain embodiments, drying comprises drying in an oven at 60° C. to 80° C. for 2 to 20 minutes. In certain embodiments, drying is carried out for 5 to 15 minutes. In certain embodiments, drying is carried out for approx. 10 minutes.

In certain embodiments, a chlorination step, in which the latex cover is exposed to chlorine, is performed after removal of the multi-layered cover from the former. In this step, residues of the coagulator liquid are removed from the outer surface of the latex cover and the outer surface is smoothened.

In certain embodiments, the former is hand-shaped.

In certain embodiments, the former is pre-warmed to approx. 60° C. prior to step b.

In certain embodiments, the particles are pre-warmed to approx. 60° C. prior to their application.

In certain embodiments, the coagulator liquid comprises sodium chloride as a coagulator. In certain embodiments, the coagulator liquid comprises acetic acid, calcium chloride, calcium nitrate, formic acid, zinc nitrate, or a mixture thereof as a coagulator.

In certain embodiments, the coagulator liquid is an aqueous solution of $Ca(NO_3)_2$. In certain embodiments, the coagulator liquid is an aqueous solution of NaCl. In certain embodiments, the coagulator liquid is an aqueous solution of $Na_2CO_3$. In certain embodiments, the coagulator liquid is an aqueous solution of $KNaC_4H_4O_6$. In certain embodiments, the coagulator liquid is an aqueous solution of $MgSO_4$.

Within the context of the present specification, the concentration of calcium nitrate and calcium carbonate is given in % (v/v). The mass of the substances weighed in ($Ca(NO_3)_2*4H_2O$ or $CaCO_3$) has been converted to a volume taking into account the density of the substances.

In certain embodiments, the concentration of calcium nitrate in the coagulator liquid ranges from 0.14% to 18.3% (v/v (the calcium part being calculated on the basis of $Ca(NO_3)_2*4H_2O$). This equals a concentration range of approx. 10 mmol/l to approx. 1.4 mol/l. In certain embodiments, the concentration of $Ca(NO_3)_2*4H_2O$ ranges from 0.5% to 3% (v/v). In certain embodiments, the concentration of $Ca(NO_3)_2*4H_2O$ is approx. 2.3% (v/v). The inventors have demonstrated that a calcium nitrate concentration of 2.3% (v/v) is preferable.

In certain embodiments, the coagulator liquid comprises a former release agent. Within the context of the present specification, the term "former release agent" refers to a substance that prevents the latex from permanently adhering to the former and enables/facilitates the removal of the multi-layered cover from the former at the end of the production process. The former release agent also prevents conglutination of the protective latex cover after removal from the former.

In certain embodiments, the former release agent is magnesium carbonate. In certain embodiments, the former release agent is sodium chloride. In certain embodiments, the former release agent is polydimethylsiloxane. In certain embodiments, the former release agent is a polyalkylene oxide modified diethylpolysiloxane. In certain embodiments, the former release agent is a stearic acid or stearate. In certain embodiments, the former release agent is selected from fatty acids, metal oxides, in particular zinc oxide, ethylenes, in particular ethylenebisoleamide, glycols, in particular polyethylene glycols and polyalkylene glycols, ammonium salts of alkyl phosphate, polyethylenes, glycerine, amorphous polypropylene, and unbranched alcohols.

In certain embodiments, the former release agent is calcium carbonate. In certain embodiments, the concentration of calcium carbonate in the coagulator liquid is approx. 10% (v/v). This equals a concentration of approx. 2.7 mol/l. In certain embodiments, the calcium carbonate is in the form of calcium carbonate particles having a mean diameter of <30 µm.

In certain embodiments, the first and second latex dispersions comprise 25% to 70% (v/v) latex. The latex may be natural or synthetic latex.

In certain embodiments, the latex content of the second latex dispersion is lower than the latex content of the first latex dispersion. This results in a second latex layer that is thinner than the first latex layer. In certain embodiments, the first latex dispersion comprises approx. 60% (v/v) latex and the second latex dispersion comprises approx. 30% (v/v) latex. In general, the use of latex dispersions with a high latex concentration results in a better separation of the first and second layers. The latex concentrations can be lower than stated above if steps c and f are repeated, i.e. performed two or three times. If step c is repeated twice, the first latex dispersion may be as low as 30% (v/v). If step c is repeated three times, the first latex dispersion may be as low as 20% (v/v). If step f is repeated twice, the second latex dispersion may be as low as 15% (v/v). If step c is repeated three times, the second latex dispersion may be as low as 10% (v/v).

In certain embodiments, the first and second latex dispersions comprise 0.2% to 5% (v/v) $NH_3$. In certain embodiments, the first and second latex dispersions comprise approx. 3% (v/v) $NH_3$.

In certain embodiments, the second latex dispersion comprises a colouring agent. In certain embodiments, the first latex dispersion comprises a colouring agent. In certain embodiments, the colouring agent is Uranin or Heliogen Blue. In the context of the present specification, the term "Uranin" refers to the disodium salt form of the compound fluorescein (CAS No. of fluorescein: 2321-07-5). Uranin is also known as "D&C Yellow no. 8". In the context of the present specification, the term "Heliogen Blue" refers to a colouring agent based on the compound specified by the molecular formula $C_{32}H_{16}CuN_8^{-4}$ (PubChem CID: 54609463). Non-limiting examples of such colouring agents are Heliogen Blue 7560, Heliogen Blue 7800, Heliogen Blue D 7490, Heliogen Blue D 7560, Heliogen Blue D 7565, Heliogen Blue G, Heliogen Blue L 7460, Heliogen Blue L 7560 and Heliogen Blue LG.

If a perforation occurs in the outer latex layer, prevailing moisture, e.g. from a wet environment or from the surrounding air, will enter through the perforation and will accumulate between the outer and inner latex layer, in other words the water/moisture will accumulate in the intermediate (particle) layer. Via capillary action, the outer and inner latex layer will visibly agglutinate/stick together and the perceived colour will be that of the inner layer. This visible effect is more pronounced if the contrast between the outer and the inner latex layer is high. In instances where a breach indicator function is desired, it is thus beneficial to include colouring agents in the outer and/or inner latex layers and/or particles. It is obvious to the skilled person that in instances where a breach indicator function is desired, both inner and outer latex layers have to be initially liquid- and air-impermeable and only become permeable if they are perforated, e.g. accidentally or by tampering.

In certain embodiments, the first and second latex dispersions comprise a vulcanization system. Addition of a vulcanization system improves hardening of the latex and provides protection against possible future deterioration of the latex. During vulcanization, the latex is modified by the formation of cross-links between individual polymer chains. In certain embodiments, the vulcanization system is a sulfur curing system. In certain embodiments, the vulcanization system comprises sulfur, zinc oxide, preservative substances and antioxidants. In instances where a vulcanization system is used, a vulcanization step is carried out following retraction of the particle treated former from the second latex dispersion in step e. The vulcanization step is carried out at a temperature between 120° C. and 200° C., in particular at approx. 140° C.

An alternative aspect of the invention relates to the method described above, wherein the second latex dispersion comprises bubbles, thus yielding a perforated second/inner latex layer. It is obvious to the skilled person that in instances where a perforated inner latex layer is desired, a breach indicator function depending on capillary action is no longer possible.

Alternatively, the method is conducted as outlined above, and a third latex layer is added. In certain embodiments, the third latex layer is applied using a latex solution comprising bubbles.

In certain embodiments, the method comprises the additional steps e2 and e3 subsequently to step e and prior to step f:

e2. Immersing the second latex covered former in a coagulator liquid to an immersion depth d3, then retracting and drying the second latex covered former.

e3. Immersing the second latex covered former in a third latex dispersion comprising bubbles, to an immersion depth d2, then retracting and drying the second latex covered former, yielding a third latex covered former.

In these instances, the method yields a multi-layered latex cover, comprising a perforated inner latex layer and a non-perforated middle and outer latex layer, the latter two supporting the breach indicator function. In step f, the word "second" is to be replaced by "third".

In certain embodiments, steps d. and e are repeated several times, yielding a multi-layered latex cover with three or more latex layers. The inner latex layer or the inner latex layer and adjacent latex layers may be intentionally perforated.

In certain embodiments, the method comprises a step d2 subsequently to step d and previous to step e, wherein step d2 comprises cleaning/stripping discrete regions from said particles (and, in instances where a second coagulator liquid was used, from said second coagulator liquid or dried remnants of it).

In certain embodiments, an adhesive cover is applied to the former after the first latex dipping, covering discrete regions and said adhesive cover is peeled off after application of the particles.

Both approaches result in discrete regions, e.g. the fingertips, that are free of particles.

The discrete particle-free regions locally avoid separation of the latex layers and the latex layers agglutinate at these discrete regions (FIG. 6). Agglutination of the layers prevents slippage and improves the tactile sense of the person wearing the glove.

In certain embodiments, the discrete regions are regions of 1 mm² to 5 cm² at each fingertip. In certain embodiments, the discrete regions are regions of 4 mm² to 2.5 cm². In certain embodiments, the discrete regions are regions of 9 mm² to 1 cm² at each fingertip. In certain embodiments, the discrete regions are regions of approx. 25 mm² at each fingertip.

In certain embodiments, the discrete regions form patterns, signs, characters or numbers.

In certain embodiments, the first and second latex dispersions and the chemically functionalized particles comprise a vulcanization system. Following retraction of the particle treated former from the second latex dispersion in step e, a vulcanization step is carried out at a temperature between 100° C. and 200° C., in particular at approx. 140° C.

In certain embodiments, steps d and e are repeated several times, yielding a multi-layered latex cover having more than two latex layers.

In certain embodiments, silica particles are employed as particles, particularly in the size ranges given previously as particular embodiments of the former.

In certain embodiments, the particles are functionalized by covalent attachment to the surface of a compound selected from 7-octenyltrimethoxysilane, 5-hexenyltrimethoxysilane, 3-mercaptopropyltrimethoxysilane, 3-amino propyl)triethoxysilane, tris(2-methoxyethoxy)(vinyl)silane, allyltrimethoxysilane, 3-(aminopropyl)triethoxysilane, hexadecyltrimethoxysilane, vinyltrimethoxysilane, triethoxyvinylsilane, 3-trimethoxysilyl-propane-1-thiol, bis [3-(triethoxy silyl)propyl]tetrasulfide, 3-(methacryloxypropyl)trimethoxysilane and 3-N-(3-triethoxysilylpropyl)gluconamide.

In certain embodiments, the particles are additionally functionalized by covalent attachment of a second compound selected from polyethylene glycol, polyglycerol, N-(3-triethoxysilylpropyl)gluconamide and 3-[methoxy (polyethylene oxy)propyl]trimethoxysilane.

The skilled person understands that the mentioned silanes will form, depending on reaction conditions, predominantly single, but also double or even triple bonds to the silica (or other solid) particle surface comprising OH moieties.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

Example 1 A

Figure 1:
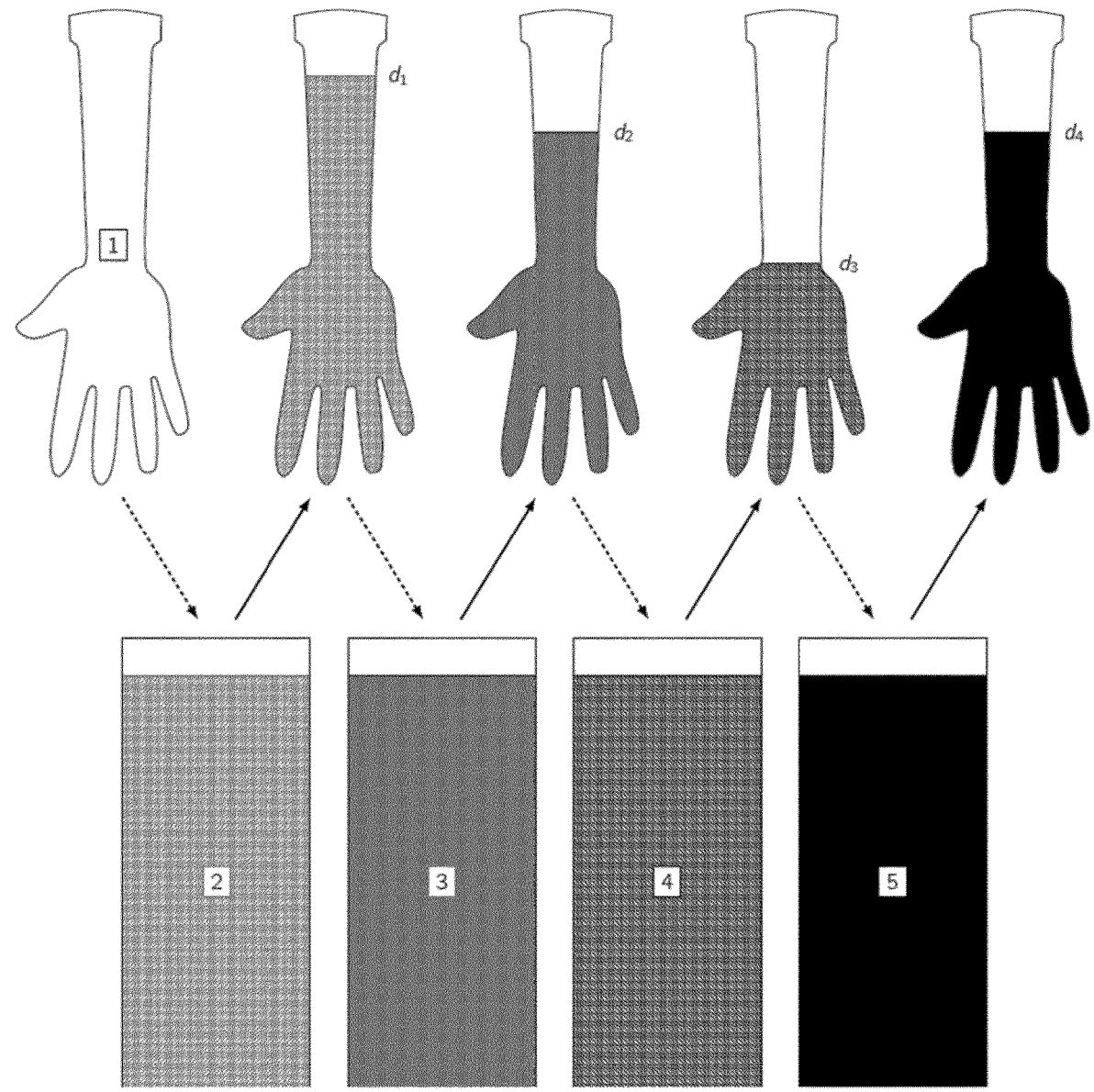
FIG. 1 illustrates the immersion depth during the dipping process. 1: former, 2: first coagulator liquid, 3: first latex dispersion/first latex layer, 4: particle suspension, 5: second latex dispersion/second latex layer, $d_1$-$d_4$: immersion depth.
Figure 2:
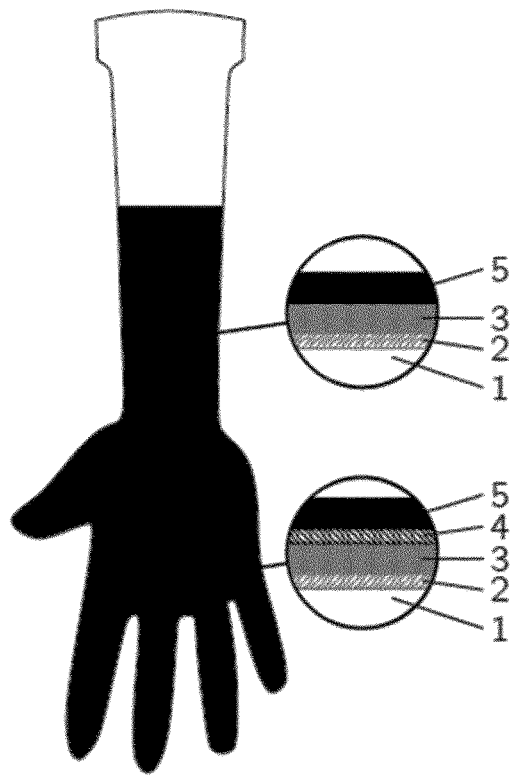
FIG. 2 shows a double-layered latex glove on a former at the end of the dipping process. The different layers of the glove are indicated in the left-hand circles. 1: former, 2: coagulator layer, 3: first latex layer, 4: particle layer, 5: second latex layer. The upper circle shows a region of the glove in which first and second latex layers are agglutinated. The lower circle shows a region of the glove in which first and second latex layers are separated.
Figure 3:
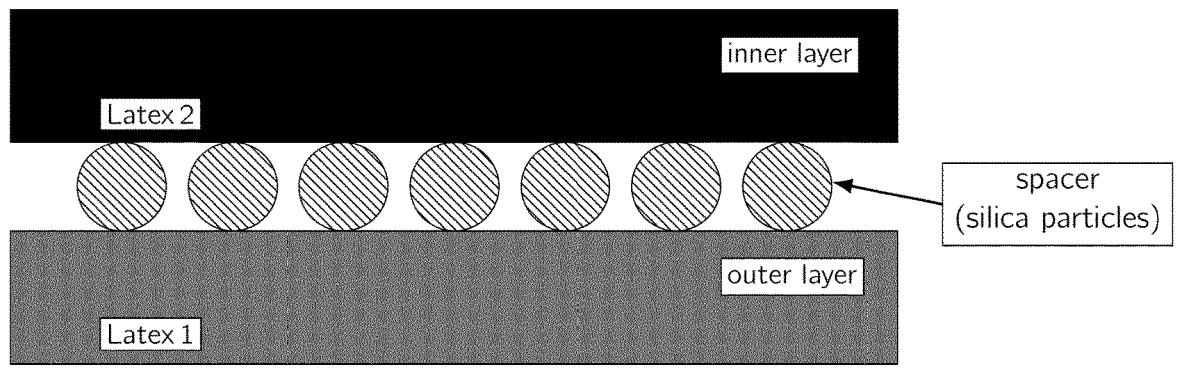
FIG. 3 shows silica particles that are positioned between inner and outer latex layer. The particles are anchored in the inner latex layer.
Figure 4:
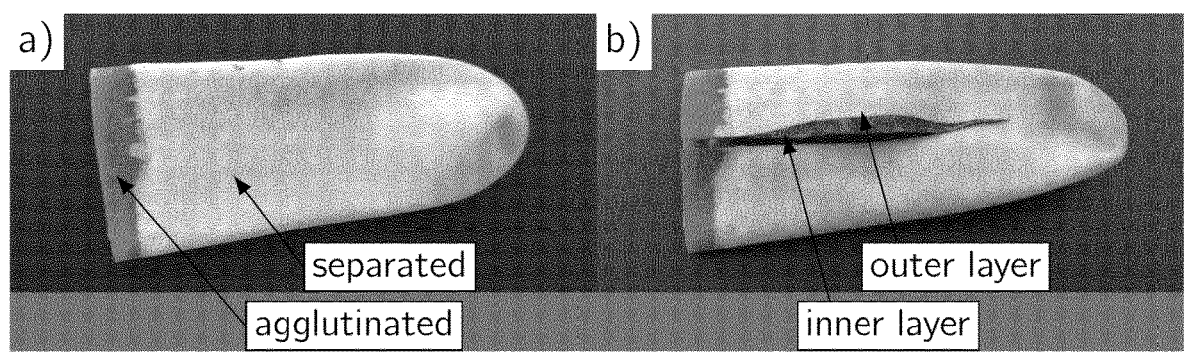
FIG. 4 shows a double layered finger cot. Arrows indicate the agglutinated and separated regions (a) and the cross-section (outer and inner layers, b).
Figure 5:
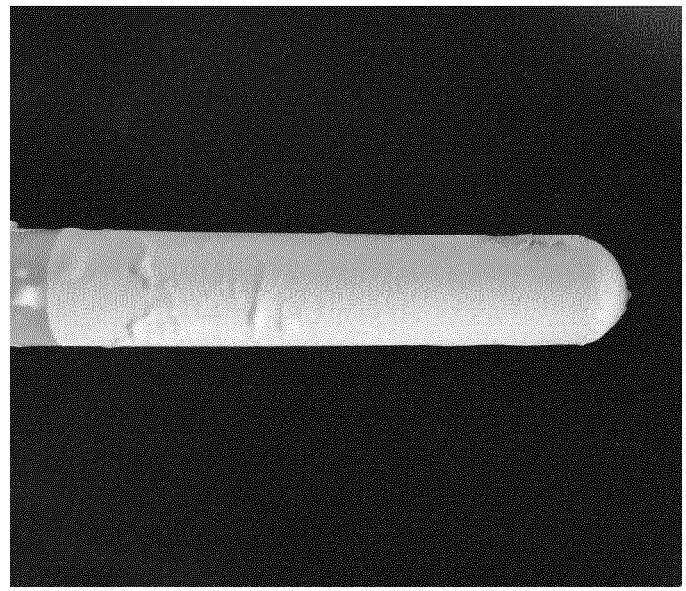
FIG. 5 shows a latex layer, which was dip-coated with functionalized silica particles and washed with a water-ethanol mixture. The particles adhere to the latex layer. This status is an intermediate step for the production of a double-layered system with particles chemically linked to one of the layers. Afterwards, this molding blank is further processed by dipping into the second latex dispersion, drying and vulcanization.
Figure 6:
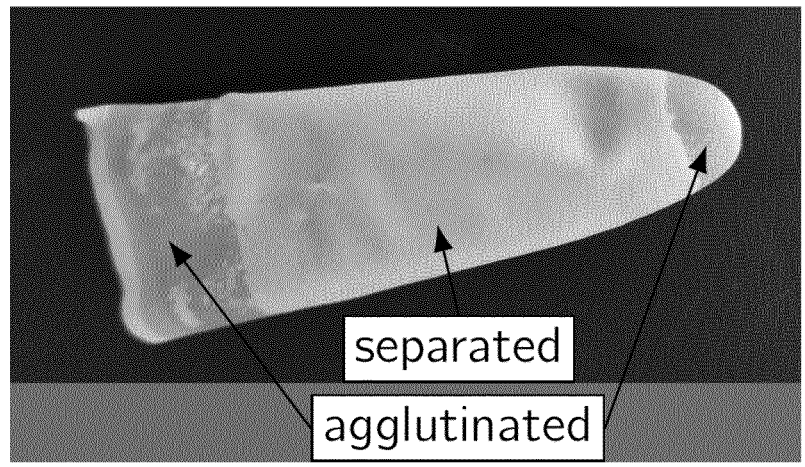
FIG. 6 shows a double layered finger cot with an agglutinated fingertip.
Figure 7:
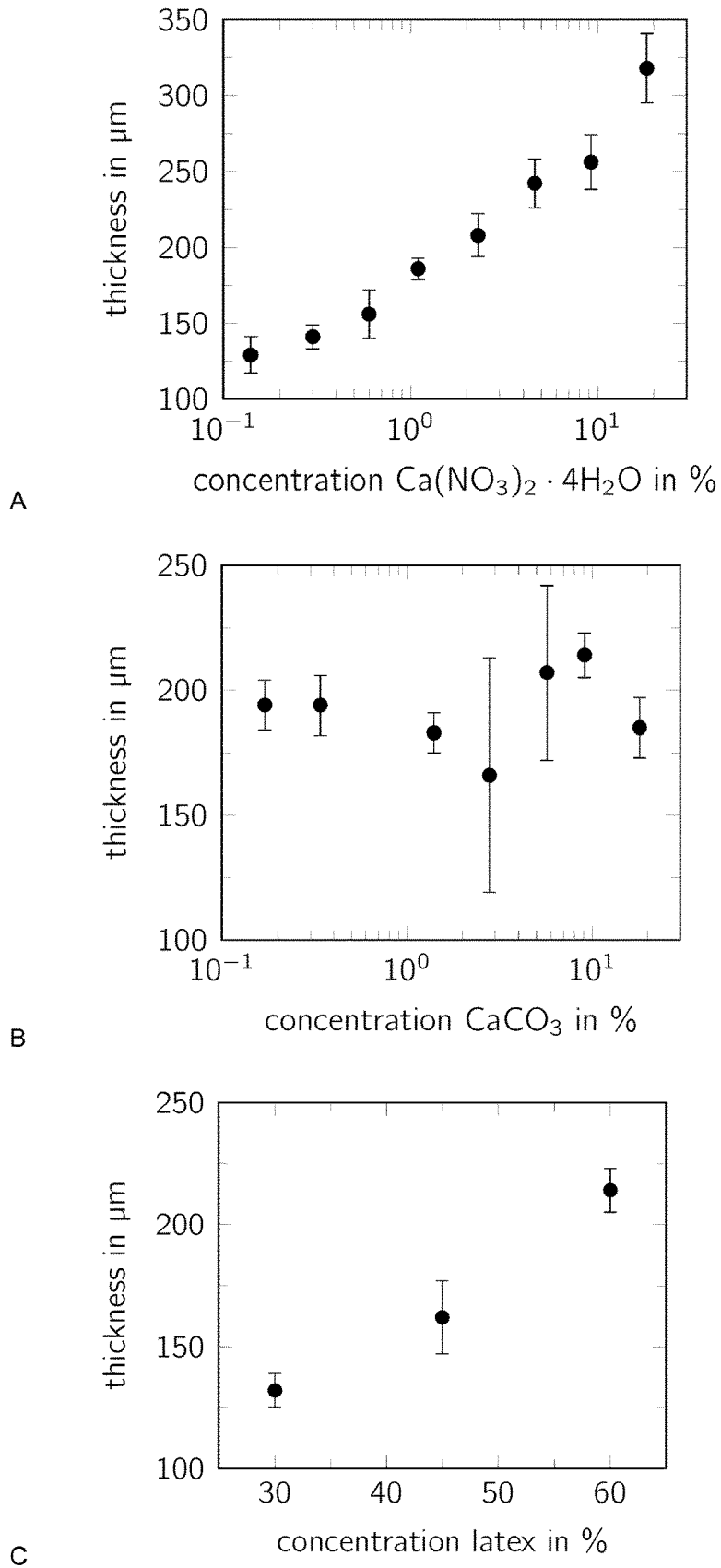
FIG. 7 shows the diagrams referred to in Example 1
Figure 8:
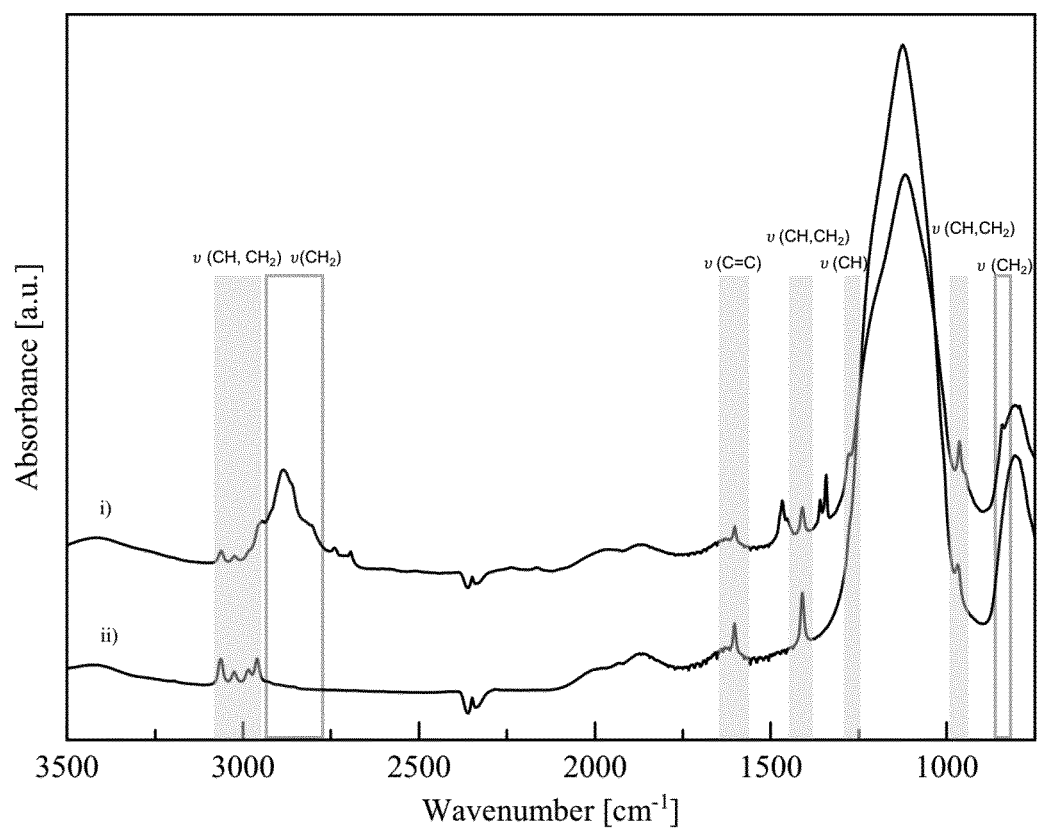
FIG. 8 shows infrared spectra measured using Diffuse Reflectance Infrared Fourier Transform Spectroscopy (in KBr pellets) of i) silica particles functionalized with triethoxyvinylsilane (VTES) and PEG2000 and ii) silica particles with VTES only. Bands of VTES (grey) and PEG2000 (white) are marked in the IR spectra.
Figure 9:
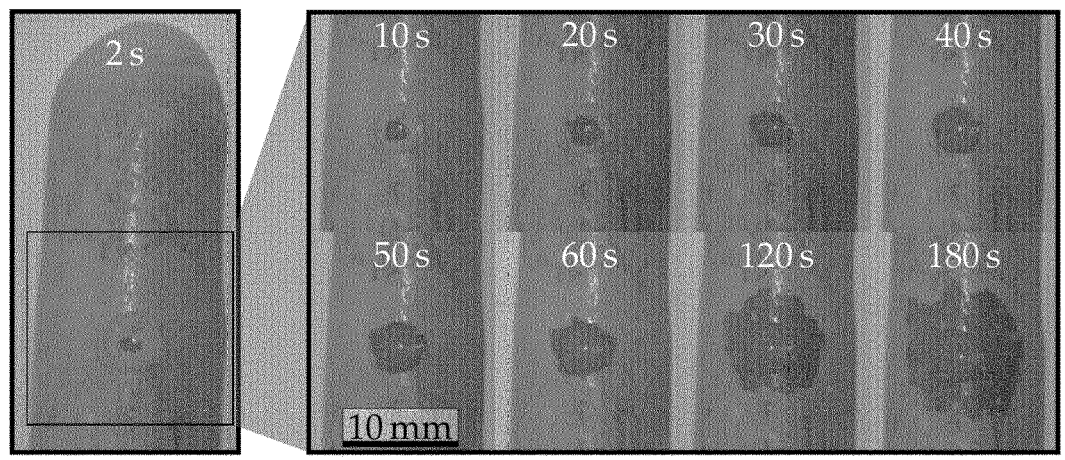
FIG. 9 shows dip-coated multi-layered covers comprising two natural rubber layers and an intermediate layer of functionalized silica particles.
  a) Time-dependent influx of a water droplet (2 s, 10 s, 20 s, 30 s, 40 s, 50 s, 60 s, 120 s, 180 s after perforation) shown for covers containing silica particles functionalized with VTES+PEG2000.
  b) Perforation indicator effectiveness (PIE, effective area of changing color over time) in dependence of surface functionalization of silica particles (triethoxyvinylsilane (VTES)+PEG2000, VTES, 3-(aminopropyl)triethoxysilane (APTES)).
c) Light-microscopy images of the cross-section of the covers showing the outer layer (1), the inner layer (2) and the intermediate layer of silica particles functionalized with VTES+PEG2000, VTES and APTES.
Figure 9:
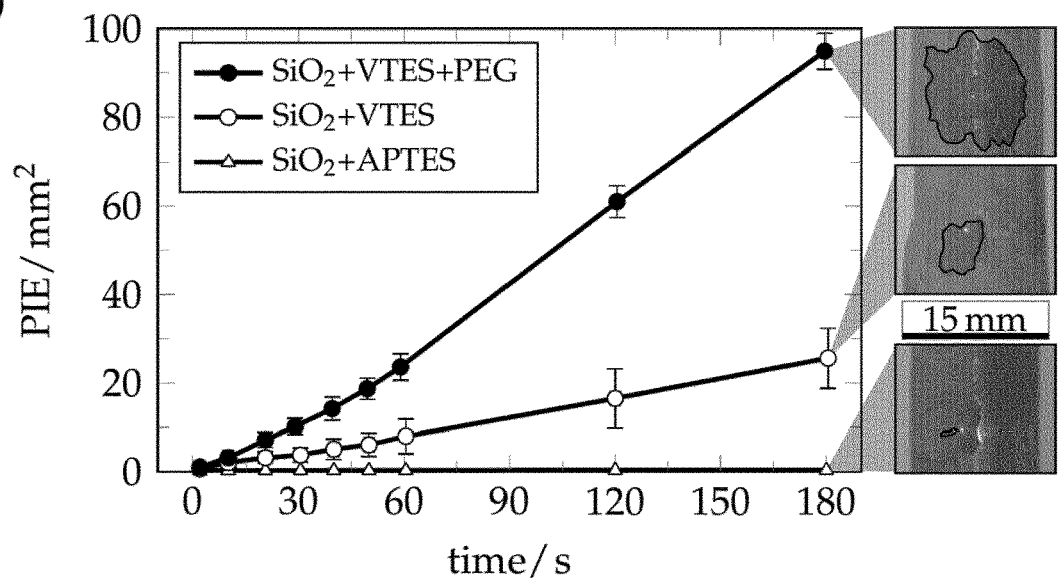
Figure 9:
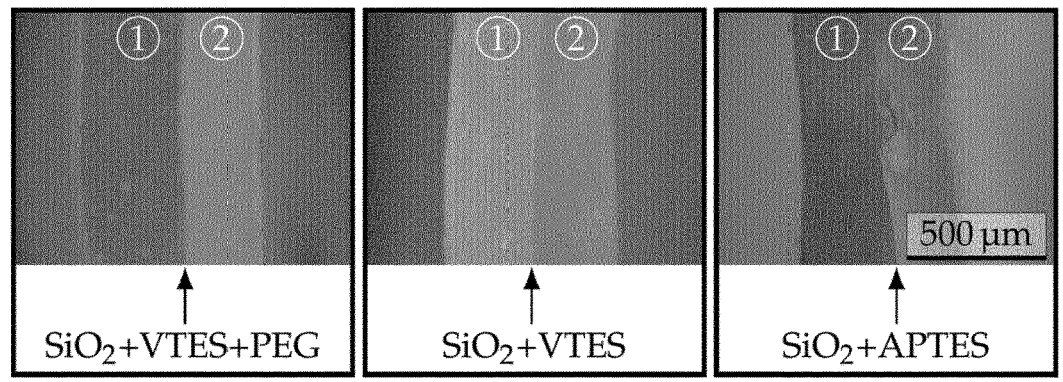
Figure 10:
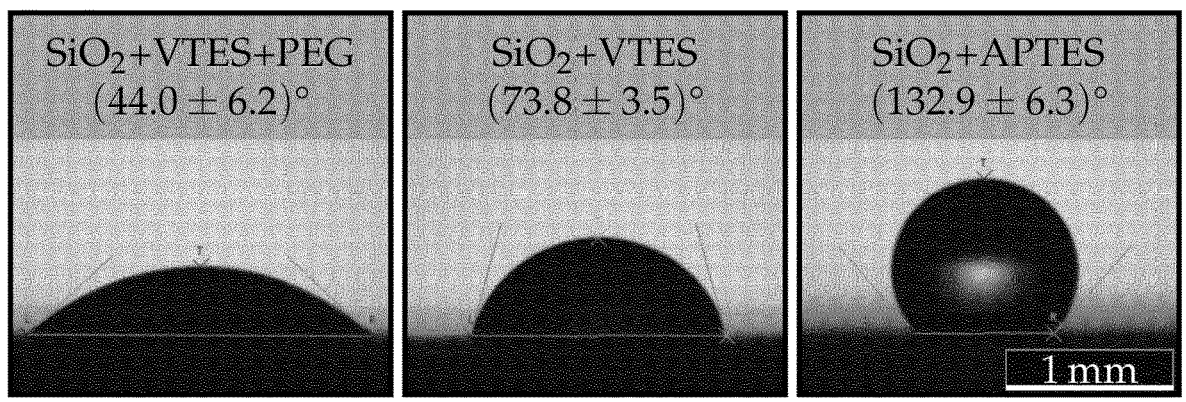
FIG. 10 exemplarily shows water droplets on natural rubber surfaces covered with functionalized silica particles and the resulting contact angle in dependence of surface functionalization of silica particles (triethoxyvinylsilane (VTES)+PEG2000, VTES, 3-(aminopropyl)triethoxysilane (APTES).

Optimization of Calcium Nitrate Concentration (Diagram FIG. 7 A)

The effect of the calcium nitrate concentration [% (v/v), calculated on the basis of $Ca(NO_3)_2 \cdot 4H_2O$] on the thickness of a single latex layer was analysed. Latex: 60% (v/v); calcium carbonate: 10% (v/v).

Example 1 B

Optimization of Calcium Carbonate Concentration (Diagram FIG. 7 B)

The effect of the calcium carbonate concentration [% (v/v)] on the thickness of a single latex layer was analysed. Latex: 60% (v/v); calcium nitrate: 2.3% (v/v).

Example 1 C

Optimization of Latex Dispersion (Diagram FIG. 7 C)

The effect of the latex concentration [% (v/v)] on the thickness of a single latex layer was analysed. Calcium carbonate: 10% (v/v); calcium nitrate: 2.3% (v/v).

Standard Protocol for Glove Production According to the Invention

1) Coagulator with release agent solution, exemplarily:
   1.5 l water
   110 g calcium nitrate
   600 g calcium carbonate ($CaCO_3$)
2) Concentration Latex 1: 30%
3) Silica particle suspension
4) Concentration Latex 2: 60%

Particle Functionalization with Silanes (exemplarily described for 1 g of particles and tris(2-methoxyethoxy)(vinyl)silane as silane)
1. Silica particles are suspended in 30 ml of Ethanol and 30 ml of NaOH solution (1 mol $l^{-1}$) and treated by ultrasound.
2. 10 ml of Ethanol, 10 ml of NaOH solution (1 mol $l^{-1}$) and 5 ml of silane are added.
3. The solution is stirred for 2 h at room temperature.
4. The particles were centrifuged and washed for two times with ethanol.
5. The suspension was dried at 30° C. for 12 hours.
6. The particles were mechanically threated to get a powder.
7. The particles are suspended in a mixture of 70% water and 30% alcohol.

Particle Functionalization with Either PEG or Silanes $SiO_2$ particles were suspended in water and mixed with the appropriate amount of silane or PEG. The pH was adjusted to 9-10 and the suspension was stirred at 75° C. for about 2-4 h. The dispersion was then dried at 75° C. for several hours to remove the solvent. The powder was then washed twice each with $H_2O$ and EtOH and centrifuged. The resulting particles were dried at 75° C. for several hours to obtain the final product.

Particle Functionalization with PEG and Silanes

As PEG, PEG200, PEG2000, PEG10000, PEG20000 and more were used. As silanes, one of the following were employed: tris(2-methoxyethoxy)(vinyl)silane, allyltrimethoxysilane, 3-(aminopropyl)triethoxysilane, hexadecyltrimethoxysilane, vinyltrimethoxysilane, triethoxyvinyl silane, 3-trimethoxysilylpropane-1-thiol, bis[3-(triethoxysilyl)propyl]tetrasulfide, 3-(methacryl oxypropyl) trimethoxysilane, 3-[methoxy(polyethyleneoxy)propyl] trimethoxysilane, N-(3-triethoxysilylpropyl)gluconamide.

The reaction was carried out as follows:

A corresponding amount of silane (10 mol % or above) was added to a suspension of silica particles in $H_2O$/EtOH (1:1 v/v). After adjusting the pH to 9-10 (NaOH or $NH_4OH$) the suspension was stirred for 5 min. Afterwards PEG (between 10 and 70 mol %) was added and the reaction mixture was stirred until PEG was dissolved. The mixture was then stirred at 75° C. for 8 h. After removing the solvent, the particles were washed with $H_2O$ and EtOH several times to remove unreacted compounds. The particles were then dried at 70° C. for 24 h to obtain the final product.

Measuring Instructions for Perforation Indicator Effectiveness (PIE)

1. Place double-layered cover on an coloured former
2. Puncture with needle
3. Place water drop on top of perforation (excess water)
4. Trigger water inflow by application of slight mechanical stress parallel to the layers (strain the perforation)
5. Take pictures with a defined length scale for calibration and after a defined period of time (2 s, 10 s, 20 s, 30 s, 40 s, 50 s, 60 s, 120 s, 180 s after perforations).
6. Quantify the PIE by measuring the affected area with image-processing, e.g. by the help of the software ImageJ (Schneider, C. A.; Rasband, W. S.; Eliceiri, K. W. (2012), Nature methods 9(7):671-675). Make sure to only consider water in between the layers, not in between latex and former.

Contact Angle Measurements

Contact angles were determined using a Kyowa Dropmeter (DMs-401) equipped with a 32 G needle from stainless steel. Drops of 2.0 µl of purified water were placed on horizontally aligned sample surfaces (sessile drop technique). A picture was taken and evaluated 10 s after surface deposition of the drop. Data acquisition and analysis was performed using the half-angle method in the interFAce Measurement and Analysis Software FAMAS.

Material

Neotex FA: natural latex, full ammonia, 60% Polyisopren with natural associated material
ProChemie-Latex: 60%, FA, Polyisopren with natural associated material
Vulcanizer: Suprotex L 4204-2, Weserland.eu
Calcium carbonate ($CaCO_3$), CAS-No. 471-34-1, S3-Chemicals
Calcium nitrate tetrahydrate ($Ca(NO_3)_2*4H_2O$), CAS-No. 13477-34-4, S3-Chemicals, 98%
Talcum powder: diacleanshop, CAS-No. 14807-96-6, EG-No. 238-877-9
Silica particles: Kremer Pigmente, spheric, <50 μm
Silica particles, fumed, CAS 112945-52-5, Sigma Aldrich 0.007 μm
Silica particles, fumed, CAS 112945-52-5, Sigma Aldrich 0.2-0.3 μm
Silica particles: Fumed silica OX50 (Aerosil®), CAS 112 945-52-5, (ex 7631-86-9)
Tris(2-methoxyethoxy)(vinyl)silane, CAS 1067-53-4, Sigma Aldrich
Allyltrimethoxysilane, CAS 2551-83-9, ABCR
3-(Aminopropyl)triethoxysilane, CAS 919-30-2, Sigma Aldrich
Hexadecyltrimethoxysilane, CAS 16415-12-06, Sigma Aldrich
Vinyltrimethoxysilane, CAS 2768-02-7, Sigma Aldrich
Triethoxyvinylsilane, CAS 78-08-0, Merck
3-Trimethoxysilylpropane-1-thiol, CAS 4420-74-0, Evonik
Bis[3-(triethoxysilyl)propyl]tetrasulfide, CAS 40372-72-3, ABCR
3-(Methacryloxypropyl)trimethoxysilane, CAS 2530-85-0, ABCR
3-[Methoxy(polyethyleneoxy)propyl]trimethoxysilane, CAS 65994-07-2, ABCR
N-(3-triethoxysilylpropyl)gluconamide, CAS 104275-58-3, ABCR
Heliogen® Blau: Kremer Pigmente, blue pigment
Uranin: Kremer Pigmente, yellow pigment
PEG 200, PEG 2000, PEG 10000, PEG 20000, CAS 25322-68-3, Carl Roth

The invention claimed is:

1. A glove for a human hand, comprising a main body and a rim, wherein
said main body comprises
a. an outer latex layer
b. an inner latex layer
c. an intermediate layer comprising particles, wherein said particles are characterized by
i. a mean diameter of ≤100 μm and
ii. a surface comprising exposed OH groups when in a non-functionalized state;
and said rim comprises an agglutinated outer and inner latex layer, characterized in that said particles are chemically functionalized with a compound comprising hydrophobic groups.

2. The glove according to claim 1, wherein said particles are inorganic particles selected from the group consisting of silica, titanium dioxide and zirconium dioxide.

3. The glove according to claim 1, wherein said particles are characterized by
a. a mean diameter of ≤1 μm, or
b. 90% of said particles having a diameter of ≤1 μm.

4. The glove according to claim 1, wherein said particles are characterized by a surface comprising exposed OH groups having a density of 2-5 $nm^2$.

5. The glove according to claim 1, wherein said compound comprising hydrophobic groups is a compound comprising
a. an unsaturated group, or
b. sulfur.

6. The glove according to claim 1, wherein said particles are additionally functionalized with a compound comprising hydrophilic groups selected from the group consisting of polyethylene glycol, polyglycerol, N-(3-triethoxysilylpropyl)gluconamide and 3-[methoxy(polyethyleneoxy)propyl]-trimethoxysilane.

7. The glove according to claim 1, wherein said functionalized particle has an amphiphilic particle surface.

8. The glove according to claim 1, wherein said particles are functionalized with at least two different compounds.

9. The glove according to claim 8, wherein
a. the first compound is suitable for yielding a hydrophobic surface, and
b. the second compound is suitable for yielding a hydrophilic surface.

10. The glove according to claim 1, wherein said particles are chemically linked to the inner and/or outer latex layer.

11. The glove according to claim 1, wherein said inner and/or outer latex layer is characterized by a contact angle with water of <90°, on a face of the latex layer facing the intermediate layer.

12. The glove according to claim 1, wherein said glove is characterized by a thickness of 100 μm to 800 μm uniformly extending across its entire dimensions.

13. The glove according to claim 1, wherein said intermediate layer comprises a plurality of double layers comprising
a. particles having a mean diameter of ≤100 μm and a surface comprising exposed OH groups, wherein said particles are chemically functionalized with a compound comprising hydrophobic groups, and
b. a latex layer.

14. A glove according to claim 13, wherein the inner latex layer, or the inner latex layer and the plurality of double layers of the intermediate layer are perforated.

15. A method of producing a multi-layered cover, comprising the steps of:
a. providing a former;
b. immersing said former in a first coagulator liquid, to an immersion depth $d_1$, then retracting and drying said former;
c. immersing said former in a first latex dispersion to an immersion depth $d_2$, then retracting and drying said former, yielding a first latex covered former;
d. applying chemically functionalized particles to said first latex covered former to an immersion depth $d_3$; yielding a particle treated former; wherein said particles are
in a non-functionalized state characterized by a mean diameter of ≤100 μm and a surface comprising exposed OH groups, and
chemically functionalized with a compound comprising hydrophobic groups;
e. immersing said particle treated former in a second latex dispersion to an immersion depth $d_4$, then retracting and drying said particle treated former; yielding a second latex covered former, wherein $d_1 \geq d_2 > d_3$ and $d_1 \geq d_4 > d_3$;

f. removing the applied layers from said coated former, yielding said multi-layered cover.

16. The glove according to claim 1, wherein said compound comprising hydrophobic groups is selected from the group consisting of 7-octenyltrimethoxysilane, 5-hexenyltrimethoxysilane, 3-mercaptopropyltrimethoxysilane, 3-(aminopropyl) triethoxysilane, tris(2-methoxyethoxy)(vinyl)silane, allyltrimethoxysilane, 3-(amino propyl)triethoxysilane, hexadecyltrimethoxysilane, vinyltrimethoxysilane, triethoxyvinyl silane, 3-trimethoxysilylpropane-1-thiol, bis[3-(triethoxysilyl)propyl]tetrasulfide, 3-(methacryloxypropyl)trimethoxysilane and 3-N-(3-triethoxysilylpropyl)gluconamide.

17. The glove according to claim 9, wherein the first compound is selected from the group consisting of 7-octenyltrimethoxysilane, 5-hexenyltrimethoxysilane, 3-mercaptopropyltrimethoxysilane, tris(2-methoxyethoxy)(vinyl)silane, allyltrimethoxysilane, 3-(aminopropyl)triethoxysilane, hexadecyltrimethoxysilane, vinyltrimethoxysilane, triethoxyvinylsilane, 3-trimethoxysilylpropane-1-thiol, bis[3-(triethoxy silyl)propyl]tetrasulfide, 3-(methacryloxypropyl) trimethoxysilane and 3-N-(3-triethoxysilylpropyl) gluconamide.

18. The glove according to claim 9, wherein the second compound is selected from the group consisting of polyethylene glycol, polyglycerol, N-(3-triethoxysilylpropyl)gluconamide and 3-[methoxy(polyethylene oxy)propyl] trimethoxysilane.

* * * * *

UNITED STATES PATENT AND TRADEMARK OFFICE
CERTIFICATE OF CORRECTION

PATENT NO. : 11,819,303 B2
APPLICATION NO. : 16/479969
DATED : November 21, 2023
INVENTOR(S) : Nikolaus Mirtschin, Martin Bothe and Larisa Schmidt It is certified that error appears in the above-identified patent and that said Letters Patent is hereby corrected as shown below:

In the Specification

Column 4 on Line 15, please remove the "m" prior to the (/)

In the Claims

Claim 4, Column 20 on Line 3, please add a (/) after 2-5, and add (^2) after nm

Signed and Sealed this
Ninth Day of July, 2024

Katherine Kelly Vidal
*Director of the United States Patent and Trademark Office*